United States Patent [19]

Allen et al.

[11] Patent Number: 5,280,079

[45] Date of Patent: * Jan. 18, 1994

[54] ABSORBENT PRODUCTS AND THEIR MANUFACTURE

[75] Inventors: Adrian S. Allen, Skipton, England; David Farrar, Portsmouth, Va.; Peter Flesher, Bingley, England

[73] Assignee: Allied Colloids Limited, England

[*] Notice: The portion of the term of this patent subsequent to Sep. 15, 2009 has been disclaimed.

[21] Appl. No.: 884,371

[22] Filed: May 18, 1992

Related U.S. Application Data

[63] Continuation-in-part of Ser. No. 521,336, May 9, 1990, Pat. No. 5,147,956, and a continuation-in-part of Ser. No. 123,572, Nov. 20, 1987, Pat. No. 4,962,172.

[30] Foreign Application Priority Data

| Nov. 20, 1986 | [GB] | United Kingdom | 8627729 |
| Apr. 10, 1987 | [GB] | United Kingdom | 8708599 |
| Apr. 10, 1987 | [GB] | United Kingdom | 8708601 |
| Apr. 10, 1987 | [GB] | United Kingdom | 8708690 |
| Aug. 4, 1987 | [GB] | United Kingdom | 8718396 |
| May 10, 1989 | [GB] | United Kingdom | 8910788 |

[51] Int. Cl.$^5$ .............. C08F 220/46; C08F 220/28; C08F 220/06
[52] U.S. Cl. ............. 525/329.2; 525/330.1; 525/919; 526/318.42; 526/240
[58] Field of Search ........ 526/318.42, 318.5; 525/330.1, 329.2

[56] References Cited

U.S. PATENT DOCUMENTS

| Re. 30,029 | 6/1979 | Smith | 128/285 |
|---|---|---|---|
| 3,311,583 | 3/1967 | Bearden | 526/318.42 |
| 3,719,647 | 3/1973 | Hardy | 260/86.1 R |
| 3,884,964 | 5/1975 | Otrhalek et al. | 560/205 |
| 3,926,891 | 12/1975 | Gross et al. | 523/412 |
| 3,980,663 | 9/1976 | Gross | 524/389 |
| 3,995,998 | 12/1976 | Rowland | 8/115.6 |
| 4,041,121 | 8/1977 | Smith | 264/191 |
| 4,057,521 | 11/1977 | Gross | 524/379 |
| 4,066,584 | 1/1978 | Allen et al. | 523/111 |
| 4,104,214 | 8/1978 | Meierhoefer | 523/105 |
| 4,351,922 | 9/1982 | Yoshida | 526/116 |
| 4,431,769 | 2/1984 | Yoshida | 524/555 |
| 4,524,186 | 6/1985 | Nagase | 525/328.8 |
| 4,725,655 | 2/1988 | Denzinger | 526/65 |
| 4,764,554 | 8/1988 | Tonge | 524/558 |
| 4,800,220 | 1/1989 | Ribba | 526/238.23 |
| 4,962,172 | 10/1990 | Allen et al. | 526/318.42 |
| 5,147,956 | 9/1992 | Allen et al. | 526/318.42 |

FOREIGN PATENT DOCUMENTS

| 0213799 | 3/1987 | European Pat. Off. . |
|---|---|---|
| 0264208 | 4/1988 | European Pat. Off. . |
| 0268498 | 5/1988 | European Pat. Off. . |
| 0272074 | 6/1988 | European Pat. Off. . |
| 2546392 | 4/1976 | Fed. Rep. of Germany . |
| 7719027 | 1/1978 | France . |
| 47-3734 | 2/1972 | Japan . |
| 56-161413 | 12/1981 | Japan . |
| 58-84819 | 5/1983 | Japan . |
| 62-69898 | 3/1987 | Japan . |
| 63-28912 | 2/1988 | Japan . |
| 783755 | 9/1957 | United Kingdom . |
| 0940766 | 11/1963 | United Kingdom . |

Primary Examiner—Joseph L. Schofer
Assistant Examiner—Mark Nagumo
Attorney, Agent, or Firm—Ostrolenk, Faber, Gerb & Soffen

[57] ABSTRACT

A water absorbent water insoluble polymeric element, such as a fibre, film, coating, bonding layer or foam, is made by forming a substantially linear polymer by polymerisation of water soluble ethylenically unsaturated monomer blends comprising carboxylic and hydroxylic monomers and then reacting the carboxylic and hydroxylic monomers in the linear polymer to form internal cross links within the polymer.

23 Claims, No Drawings

ABSORBENT PRODUCTS AND THEIR MANUFACTURE

This application is a continuation-in-part application based on application Ser. No. 07/521,336, filed May 9, 1990 now U.S. Pat. No. 5,147,956 which was a continuation-in-part of application Ser. No. 07/123,572, filed Nov. 20, 1987 and U.S. Pat. No. 4,962,172.

This invention relates to water absorbent, water insoluble, polymeric elements that are useful for absorbing aqueous fluids, for instance urine.

It is well known to provide water absorbent, water insoluble, polymeric material in the form of particles by polymerising water soluble monomer or monomer blend, for instance acrylic acid, in the presence of a polyethylenically unsaturated monomer, that will be copolymerised into the polymeric backbone so as to cause cross linking and render the polymer insoluble in water. Ionic cross linking, for instance by aluminium ions, between pendant groups is also known. Since the cross linking occurs substantially simultaneously with the polymerisation, the normal methods do not permit the polymer to be shaped by extrusion or coating techniques after polymerisation. Instead it is made in its desired final shape, e.g., as beads by reverse phase polymerisation, or in bulk form and is then comminuted to particles. There are, however, many instances where it would be desirable to be able to provide the polymer in the form of a film, fibre or other shaped element.

In U.S. Pat. Nos. 3,926,891, 3,980,663 and 4,057,521 various processes are described in which a substantially linear acrylic polymer is shaped and is then cross linked through its pendant groups. In U.S. Pat. No. 3,926,891 and 3,980,663 a shapable solution of substantially linear acrylic polymer is formed, a cross linking agent is mixed into the solution, the solution is shaped and then the cross linking reaction is performed. In practice the method is not very successful. It seems to be difficult or impossible in practice to achieve uniform distribution of the cross linking agent in the polymer solution (which is usually relatively viscous) and, in any event, during the shaping and cross linking operations the cross linking agent is liable to migrate through the solution, and the degree of cross linking is difficult to control accurately. Accordingly it has apparently been difficult or impossible to obtain products having a controllable and uniform degree of water adsorption by this technique.

In U.S. Pat. No. 4,057,521 it is proposed that the linear polymer should be a copolymer of, for instance, acrylic acid and N-methylol acrylamide, with the intention that cross linking should be caused, after shaping of the solution, by condensation of a carboxylic acid group with the methylol acrylamide group. It is proposed that the condensation would result in the elimination of a molecule of water, and thus the formation of an ester linkage containing a nitrogen atom in the linkage. In practice however other reactions will certainly occur in parallel with it, and possibly in preference to it. In particular there will inevitably be significant formation of bis-acrylamide groups, with liberation of formaldehyde. The presence of such groups, and the liberation of formaldehyde, renders the process unacceptable for many of the uses of water absorbent polymeric materials, for instance in diapers.

Another apparently unsuccessful proposal is made in FR 2,355,929. In this, a diol or diamine is mixed into an aqueous solution of polyacrylic acid which is then shaped and the shaped article is heated to cause condensation between the difunctional cross linking agent and the polyacrylic acid. Again, this suffers from the same disadvantages of difficulty of achieving a uniform distribution of the cross linking groups through the polymer.

Comonomers that have been mentioned in these patents include certain hydroxyalkyl acrylate monomers, but they appear to be unreactive during the described processes.

In addition to these proposals that have, apparently, not been commercialised, various shaped absorbent particles have been made, especially in the form of films or fibres.

One type of absorbent fibre is formed by hydrolysing the outer surfaces of polyacrylonitrile fibres so as to form a sheath of linear water soluble polymer and a core of insoluble polymer that gives the fibre strength. Another process comprises precipitating a water soluble polymer onto an insoluble substrate such as cotton (see e.g. U.S. Pat. Nos. 4,041,121 and 4,218,692). Another process involves injecting an aqueous solution of water soluble polymer into a stream of viscose just prior to extruding the viscose as a fibre or filament (see e.g. U.S. Pat. Nos. 4,066,584, 4,104,214 and Re30,029). All these methods suffer from the disadvantage that the fibres incorporate a substantial amount of a material (polyacrylonitrile, viscose or cotton) that is of low absorbency and so the capacity of the fibres, on a weight basis, is relatively low compared to existing absorbent polymers. Also the soluble surface of many of the fibres tends to cause stickiness during use.

In practice therefore it has proved difficult or impossible to make or handle films or fibres of appropriate water absorbent polymeric material on large scale manufacturing equipment, and the absorbency and other performance properties of the films and fibres tends to be inferior compared to conventional particulate absorbent polymers.

There remains an urgent need for fibres, films or other shaped articles of water insoluble water swellable polymer that can be made reliably by large scale, high speed, manufacturing processes and that have satisfactory absorbency properties compared to the absorbency properties of conventional particulate water swellable polymers.

A water absorbent, water insoluble, polymeric element according to the invention is an element that has been made by forming a substantially linear polymer by polymerisation of a water soluble ethylenically unsaturated monomer blend comprising monomer that provides carboxylic acid monomer groups and monomer that provides hydroxylic groups that can react with the carboxylic acid groups to form ester linkages that contain only carbon and oxygen atoms in the linkages, and then reacting the said carboxylic and hydroxylic groups to form the said cross linkages.

The invention therefore eliminates the need to incorporate an external cross linking agent into a solution of pre-formed linear polymer, and instead cross linking is obtained by reaction between pendant groups on the pre-formed polymer. The instability and other undesirable consequences of relying upon groups such as methylol acrylamide is avoided by utilising monomers that do not incur the risk of, for instance, formaldehyde liberation and that, instead, react to form ester cross linkages that are free of nitrogen atoms in the linkage and that, instead, contain only carbon and oxygen atoms in the linkages. Such linkages appear to be entirely satisfactory from the toxicological point of view.

However the main advantage of the invention is that it is possible, for the first time, conveniently to make the substantially linear polymer in any convenient manner (for instance as a bulk solution) and then to shape the substantially linear polymer into a desired final shape, and then to effect the cross linking in a very controlled manner to give a product that is toxicologically entirely acceptable. Generally therefore the substantially linear polymer is made in solution, generally aqueous solution, and this solution is shaped before the formation of the cross linkages. The monomers used for providing the cross links must therefore be such that it is possible to form the polymer and to shape the polymer without cross linking occurring, and to cause substantially complete cross linking by appropriate treatment of the shaped polymer.

Suitable carboxylic monomers are (meth) acrylic acid or any of the other conventional ethylenically unsaturated carboxylic acids, optionally with 2-acrylamido-2-methyl propane sulphonic acid or any of the other conventional ethylenically unsaturated sulphonic acids, or allyl sulphonate. Carboxylic and sulphonic monomers may be present in the final polymer in free acid or water soluble salt form, suitable salts being formed with ammonia, amine or alkali metal. The proportion of salt and free acid groups can be adjusted after formation of the cross linked polymer or after polymerisation of the linear polymer or before polymerisation. Generally the ratio of free carboxylic acid/alkali metal or other salt carboxylic acid groups in the final polymer (and often also in the monomers that are used to form the linear polymer) from 1:1 to 1:10. The ratio is usually at least 1:2 and often 1:3. It is generally below 1:6 and often below 1:5.

In many instances it is desirable, in order to promote the internal cross linking reaction, that some at least of the carboxylic acid groups should be present as free acid groups before the cross linking occurs. For instance, for this purpose, it may be adequate for 10 to 75%, preferably 25 to 75%, of the acid groups to be in free acid form before the cross linking occurs.

Although the linear polymer is generally made by polymerisation of carboxylic acid monomer (in free acid or salt form) it is also possible to make the polymer be polymerisation of monomer that can be subsequently reacted to form the carboxylic acid monomer. For instance the carboxylic acid (as free acid or salt form) group that are to be present in the cross linked monomer may be present initially in the linear polymer in the form of hydrolysable ester groups, such as methyl ester groups, that can then be hydrolysed while in the form of a linear polymer to yield carboxylic acid (free acid or salt) groups.

The monomer that provides hydroxylic groups for internal esterification with the carboxylic acid groups is selected from ethylenically unsaturated monomers that can react with carboxylic acid groups to form the desired ester linkages. The monomer must be one that does not form the ester cross links during the initial polymerisation to make the linear polymer, and that does not form any substantial number of cross links during the shaping of the linear polymer.

The hydroxyl groups may be generated in the linear polymer by, for instance, breaking a ring such as a glycidyl or epoxide substituted vinyl monomer, but preferred monomers contain free hydroxyl groups and are selected from vinyl alcohol, allyl alcohol and hydroxy alkyl esters of vinyl carboxylic monomers. The preferred esters are hydroxy alkyl esters of (meth) acrylic acid. The monomer may be monofunctional, containing a single hydroxyl group, or may be polyfunctional, containing two, three or more hydroxyl groups per vinyl group. The hydroxyl alkyl group generally contains from 1 to 10, preferably 1 to 8, carbon atoms. Suitable monomers include hydroxy ethyl (meth) acrylate, hydroxyl propyl (meth) acrylate di- or tri-alkylene glycol mono (meth) acrylate where the alkylene group is ethylene or propylene, and glyceryl mono (meth) acrylate.

The amount of hydroxy monomer is preferably 0.1 to 15%, generally 1 to 10%, and the amount of carboxylic acid (or salt) is preferably above 50%, and often above 70%. These amounts are by weight based on total monomers. Often the blend is formed of 90-99% acrylic acid (some being in salt form) and 1 to 10% hydroxy alkyl acrylate.

Polymers formed solely from the defined carboxylic acid (as free acid and/or salt) and hydroxyl monomers tend to be rather brittle and it is preferred to include in the polymer plasticising monomers. The use of hydroxy alkyl esters containing 6 to 10 carbon atoms will promote plasticisation but it is generally desirable to include additional plasticising monomer so as to promote plasticisation and improve flexibility of the resultant polymer. The monomers may be aromatic ethylenically unsaturated monomers, such as acrylonitrile or styrenes (e.g., styrene or substituted styrenes), but they are preferably alkyl esters of (meth) acrylic acid or other suitable unsaturated carboxylic acid. Vinyl acetate and other vinyl esters may be used. The alkyl group of the ester generally contains less than 24 carbon atoms and usually 2 or more. Preferred alkyl groups contain 1 to 10 carbon atoms, especially ethyl and also higher alkyl groups such as 2-ethyl hexyl or other C6–C10 alkyl groups. Particularly preferred plasticising monomers are methyl or ethyl (meth) acrylate, butyl (meth) acrylate and 2-ethyl hexyl (meth) acrylate. They are generally present in amounts of at least 2% and often at least 10%. The amount is usually below 50%, and generally below 45%, by weight based on the monomers used for forming the substantially linear polymer.

Other non-ionic monomers that may be used include ethylenically unsaturated monomers that carry a pendant group $-A_mB_nA_pR$ wherein B is ethyleneoxy, n is an integer of at least 2, A is propyleneoxy or butyleneoxy, m and p are each an integer less than n and preferably below 2 and most preferably zero, and R is a hydrophobic group containing at least 8 carbon atoms. The use of 1 to 50% by weight, generally 5 to 30% by weight, of such monomers can give plasticisation and can give improved absorptive capacity and non-tackiness, especially in aqueous electrolytes.

For a full description of suitable values of A, B R, n, m and p, reference should be made to EP 0213799.

The substantially linear, water soluble, polymer may be formed from the monomer blend in any conventional manner. It may be pre-formed and then dissolved to form a polymer solution. For instance it may be made by reverse phase polymerisation if the monomer blend is soluble in water or by water-in-oil emulsion polymerisation if the blend is insoluble in the water, e.g., at a low pH. However this can incur the risk that the polymer may be contaminated by surfactant and this is undesirable. Preferably therefore the polymer is made by aqueous solution or other solution polymerisation methods. It may have been dried, but preferably not. Generally it is formed by solution polymerisation in the solvent in which it is to be shaped (generally water).

The polymerisation can be conducted in conventional manner in the presence of conventional initiators and/or chain transfer agents to give the desired molecular weight. If the molecular weight of the linear polymer is too low, the physical properties of the article may be inadequate. Generally therefore it is at least 30,000 and preferably at least 100,000 when the article is an extruded film or fibre but lower values, e.g., down to 10,000 or even down to 3,000 may be suitable in some shaping process, e.g., for casting or coating. If the molecular weight if too high it may be difficult to shape an adequately concentrated solution of the polymer as a fibre or film. Generally the molecular weight is below 1 million, usually below 500,000 and preferably below 250,000. However where the shaped article can initially be relatively, thick, e.g., a coarse film or fibre that may then be stretched if it is desired to reduce its thickness, higher molecular weights, e.g., up to 10 million or more, are sometimes suitable.

Preferably the substantially linear polymer is, at the time of cross linking, substantially free of unreacted hydroxyl-providing monomer or other cross linking agent. The polymerisation should therefore be conducted in known manner so as to give substantially no free monomer in the polymer solution. The polymer solution generally is a solution in water or in organic solvent (e.g., methanol) or a blend. Preferably the solvent is water. The polymer concentration is generally at least 5% and is usually below 50%. Often it is 10 to 40% and typically is 20 or 25% to about 35%.

After formation of the linear polymer, it is shaped and the cross linking reaction is then caused to occur.

The invention is of particular value when the shaping is by extrusion of the solution of the substantially linear polymer to provide a shaped element that has one dimension at least five times a second dimension. For instance films and fibres can be made. This shaping can involve coating the solution on a surface but generally comprises extruding it as a film or fibre. Substantially immediately after extruding or otherwise shaping the solution, the linear polymer reagent is caused to form a uniform solid mixture in the form of an article of the desired shape. The article is initially generally very soft. The conversion of the liquid solution to the soft solid articles can be described as precipitation and may involve solvent evaporation, solvent extraction, or other means of insolubilising the polymer.

The shaping can be by wet spinning into an organic solvent that removes water, generally acetone, methyl ethyl ketone or other lower ketone, or into an inorganic aqueous salt solution such as of lithium chloride or aluminium sulphate. Acetone is preferred.

Alternatively it can be by dry spinning. Preferably it remains slightly damp until the final cross linking in order to maintain softness. In a particularly preferred method, an aqueous solution of the linear polymer is dry spun at a temperature above 150° C., often above 200° C., typically 220° to 270° C. to give a product that is substantially dry on the surface but contains at least 10% residual moisture, the dry spun product is stretched and is cured by heating, generally after collecting the stretched fibre or film.

Cross linking can be promoted by incorporating a catalyst in a solution of the polymer or by exposing the shaped polymer to a catalyst (e.g., by passing the polymer through an atmosphere or solution of a catalyst for the esterification reaction). Generally however the esterification is conducted in the absence of added catalyst. The monomers can be selected such that the esterification is effected by irradiation but generally it is effected by heating the shaped substantially linear polymer to a temperature above 150° C. for sufficient time for the cross linking reaction to occur. For instance it may be 170° C. to 200° C. for 5 to 40 minutes. At higher temperatures shorter reaction times are appropriate, for instance 0.1 to 10 minutes at 200° to 250° C. or up to 300° C. Preferred esterification conditions generally involve heating to 200° to 220° C. for, for instance, 1 to 3 minutes.

Additional components may be included in the solution that is to be shaped in order to modify the properties of the final product. For instance, external plasticiser may be incorporated. The amount of material other than the cross-linked polymer is generally below 20%, preferably below 10%, by weight of the final article.

The shaped element often has a minor dimension (e.g., the thickness of the film or diameter of fibre) below 1 mm, usually below 500 µm and preferably below 250 µm. However it is usually unnecessary for it to be smaller than 50 µm. The element can have a relatively short major dimension, for instance 1 mm, e.g. in a fibrid, lamella or flake shaped article but generally the final element is a substantially continuous film, a substantially continuous filament, or staple fibre typically having a length of 3 to 100 mm.

The element usually has a gel capacity of at least 50 g deionised water, and at least 20 g 0.9% NaCl aqueous solution, per gram dry polymer.

The element may be provided with additional surface cross-linking, for instance ionic cross-linking with aluminium or other polyvalent metal compound, in order to improve its rate of absorption of liquids.

The resultant absorbent elements may be used in any environment where it is desirable to absorb water, and in particular aqueous electrolyte such as urine or other body fluids, for instance as a replacement for part of the cellulosic fibres in diapers, catamenial appliances, incontinence pads or bandages. When the articles are in the form of fibres they may be scattered into the cellulosic fibres or a film or, preferably, a woven or nonwoven fabric formed of the filaments or fibres may be incorporated in the diaper or other article.

Wound dressing, absorbent wipes and other fabrics may be formed from fibers part or all of which are in accordance with the invention.

In another method the shaping is by impregnating or coating a solution of the substantially linear polymer on to a film or fibrous core. Thus an absorbent product according to the invention is a fibrous or film product comprising a core and a surface layer of a cross linked, absorbent, polymer formed by cross linking the linear polymer in the manner described above.

The product may be made by sizing the core, as a fibrous or film product, in a solution of the linear polymer, and then cross linking the linear polymer.

The core may be a film but is generally fibrous. It may be a continuous filament or a yarn. It may be formed of, for instance, cotton yarn or it may be a yarn, filament or film or polyester, polypropylene, acrylic, polyamide or other polymeric material.

The dry pick up to the sizing polymer typically is 2-25%, preferably 7-17% by weight.

The linear polymer preferably forms a discontinous film on the core (so as to improve flexibility) and good results are obtained when the core has a relatively hydrophobic surface and the size is aqueous. Preferably the core is of polyester yarn, filament or film.

Woven or non-woven sheet materials can be sized.

The sized products of the invention can be used in the manufacture of absorbent liners, clothing or fabrics or in the manufacture of articles such as disperse or wound dressings. Sized fibres or yarns can be incorporated into a wide variety of fibre blends in amounts of, e.g., 0.05 to 20% by weight, or articles may be formed solely from the sized fibres. Liners of the invention may be used for food, flower or vegetable packaging, especially in ice packages. It may be used as a horticultural growing medium.

Another absorbent product according to the invention comprises a sheet substrate and an absorbent substrate bonded to it by a cross linked absorbent polymer formed by cross linking the linear polymer in the manner described above.

The product may be made by laminating the absorbent substrate to the sheet substrate while either or both of the facing surfaces of the substrate carry a coating of the linear polymer and then cross linking the linear polymer while bonding the facing surfaces with the polymer.

The linear polymer may initially be dry and may then be wetted and cross linked so as to cause adhesion and cross linking. Generally the linear polymer is applied as a solution and the substrates laminated while one or both of the facing surfaces are wet.

The linear polymer may be applied as an overall coating, e.g., by spread coating or spray, or as a discontinuous coating, e.g., by spray or printing. A pattern of lines or dots, with uncoated areas in between is often particularly useful.

Other absorbent material, e.g., swellable polymer particles of fibres, may be bonded between the substrates by the polymer.

Generally both substrates are absorbent. Generally both are fibrous, often non-woven. Preferably both are paper tissue. If desired one may be formed by depositing fibres on to the other, after application of the polymer. Conveniently the polymer is applied as a laminating solution during the manufacture of laminated paper, in conventional manner.

The product may therefore be used as a laminated kitchen or industrial wipe or as a paper towel or as a wound dressing. It may be used as an absorbent liner, e.g., in diapers or in food, flow or vegetable packaging, especially in ice packages. It may be used as horticulatural growing medium.

The amount of linear polymer is generally from 1 to 50% by weight of the laminate (when dry).

Another absorbent product according to the invention comprises a foam having the absorbent polymer substantially uniformly distributed throughout the foam. The foam may consist of the polymer or the polymer may be incorporated in a supporting foam of some other polymeric material, for instance a polyurethane. Thus the shaping may be effected by incorporating a solution of the substantially linear polymer into a foamable composition foaming the composition and cross linking the polymer. Preferably the foamable composition comprises a foamable polymer-forming material preferably a polyurethane prepolymer that preferably is hydrophiclic, preferably a polyether polyisocyanate. The amount of the linear polymer typically is 0.03-1, generally 0.05-0.5, parts per part by dry weight of the final dry weight of the foam.

The foam can be used for various absorbent purposes. For instance it may be comminuted and included as part of the absorbent in diapers.

Although the use of hydroxy propyl (meth) acrylate as the hydroxylic monomer frequently gives a product that has satisfactory absorption characteristics, the results can be rather variable and it would be desirable to be able to obtain higher absorption characteristics more reproducibly.

We have surprisingly found that it is possible to achieve this if the hydroxyl-containing monomer is based on a polyalkylene glycol containing at least 5 oxyalkylene groups.

A water soluble substantially linear polymer according to this aspect of the invention is formed by copolymerisation of a water soluble blend of monoethylenically unsaturated monomers comprising carboxylic monomer that provides carboxylic groups and hydroxylate monomer that provides hydroxyl groups and that has the formula $CHR^1=CR^2-Y-M_a-OH$ where $R^1$ is hydrogen or carboxy, $R^2$ is hydrogen, carboxy or methyl, Y is O, $CH_2O$ or COO, M is alkyleneoxy and a is at least 5, and the linear polymer is capable of being cross linked by esterification of the said carboxyl groups with the said hydroxyl groups.

A water absorbent, water insoluble polymer according to the invention is formed from this substantially linear polymer by esterification of the carboxyl and hydroxyl groups to form cross linkages of the formula $-Y-M_a-OCO-$, where Y, M and a are as defined above. The absorbent polymer is highly absorbent and generally has a gel capacity of at least 50 grams deionised water per gram dry polymer.

Since the polymer is water insoluble and water absorbent, it will be present in the form of shaped elements such as particles, films, fibres, or coatings. The linear polymer can be formed by polymerisation in the shape of the desired elements, for instance by reverse phase bead polymerisation to make beads in the general manner described in Chemical Abstracts 96:163649q, and the linear polymer is then caused to undergo esterification to form the desired cross links.

Preferably however the linear polymer is formed and is then shaped into the shape of the desired elements, and is then subjected to the esterification.

The shaped elements, especially those formed by shaping the linear polymer and then effecting the esterification, the methods of producing the shaped elements, and solutions of the linear polymer form further parts of the invention.

By the invention it is possible to achieve higher and more reproducible adsorption characteristics in the final absorbent polymers than were possible in the polymers described above. Although we do not wish to be bound by theory, we think that the extent of cross linking was rather variable because it was difficult for the hydroxyl groups reliably to react with carboxyl groups was low and their chain length was short. There was therefore a significant risk that a hydroxyl groups was low and their chain length was short. There was therefore a significant risk that a hydroxyl group in one chain would not be in the correct steric position to esterify with the carboxylic group in another chain and it would, instead, either remain unreacted or esterify with the carboxylic group in the same chain. By providing a much longer linkage between the chain and the hydroxylic group it seems that we probably improve significantly the statistical chances of the hydroxyl group locating the esterifying with a carboxyl group of another polymer chain.

If this theory is right, it might have been observable to a small extent in example 4 below, when using tripropylene glycol monoacrylate. However this material is, as mentioned above, commercially always contaminated with tripropylene glycol diacrylate and so the material that we used would have contained diethylenically unsaturated monomer and this would have interfered with the formation of the desired linear polymer, possibly resulting in cross linking at that stage. In the invention, it is necessary that the blend of ethylenically unsaturated monomer should consist essentially only of monoethylenically unsaturated monomer, and in particular that it should not be contaminated by accidental or deliberate incorporation of di- or poly-ethylenically unsaturated monomer.

When Y is oxygen the hydroxyl-containing monomer can be regarded as a derivative of a vinyl alcohol and when Y is $CH_2O$ the monomer can be regarded as a derivative of an allyl alcohol. Preferably however Y is COO in which event the monomer can be regarded as an acrylate. The monomer may be a hydroxy polyoxy alkylene ester of, for instance, itaconic acid, furmaric acid, maleic acid, methacrylic acid, crotonic acid or, preferably acrylic acid. Preferably $R^1$ is hydrogen and $R^2$ is methyl or, most preferably hydrogen.

The groups M can be selected from propyleneoxy, ethyleneoxy, butyleneoxy or other suitable alkylenoxy groups, but preferably some or all of them are propyleneoxy. If mixed alkyleneoxy groups are present then they may be distributed randomly or in blocks along the alkyleneoxy chain. The alkyleneoxy chain preferably contain at least 6 alkyleneoxy groups and a can be up to 100 or even 200 but often there is not advantage in having more than 10, or at the most 20, alkleneoxy groups in the chain.

It is particularly preferred that the alkyleneoxy chain contains at least 6 propyleneoxy groups, for instance being based on hexapropylene glycol.

The hydroxylic monomer can be a commercially available material or can be synthesised in known manner, for instance by polycondensing alkylene oxide on to acrylic acid or other monomers of the formula $CHR^1=CR^2-YH$. If the monomer is made by condensing a preformed polyalkylene glycol on to the monomer $CHR^1=CR^2-YH$ then it is preferred that one of the hydroxy each groups of the polyalkylene glycol should be blocked before the reaction, e.g., by methyl, so as to minimise the formation of di-unsaturated monomer. The blocking group should then generally be removed before the internal esterification reaction and generally it is removed before the formation of the linear polymer, and generally before the monomer is introduced into the water soluble blend of monomers.

However the invention does, of course, also include polymers formed by internal esterification between the carboxyl and hydroxyl groups when either or both of them are blocked by a group that is removed during the esterification, provided that the blocking group (for instance a methyl ester group on the carboxylic or a methyl ether group on the hydroxyl) does not prevent the internal esterification reaction occurring.

Suitable carboxylic monomers are (meth) acrylic acid or any of the other conventional ethylenically unsaturated carboxylic acids, optionally with 2-acrylamido-2-methyl propane sulphonic acid or any of the other conventional ethylenically unsaturated sulphonic acids, or allyl sulphonate. Carboxylic and sulphonic monomers may be present in the final polymer in free acid or water soluble salt form, suitable salts being formed with ammonia, amine or alkali metal. The proportion of salt and free acid groups can be adjusted after formation of the cross linked polymer or after polymerisation of the linear polymer or before polymerisation. Generally the ratio of free carboxylic acid/alkali metal or other salt carboxylic acid groups in the final polymer (and often also in the monomers that are used to form the linear polymer) from 1:1 to 1:10. The ratio is usually at least 1:2 and often 1:3. It is generally below 1:6 and often below 1:5.

In many instances it is desirable, in order to promote the internal cross linking reaction, that some at least of the carboxylic acid groups should be present as free acid groups before the cross linking occurs. For instance, for this purpose, it may be adequate for 10 to 75%, preferably 25 to 75%, of the acid groups to be in free acid form before the cross linking occurs.

The amount of hydroxyl monomer is preferably 0.1 to 15%, generally 1 to 10%, and the amount of carboxylic acid (or salt) is preferably above 50%, and often above 70%. These amounts are by weight based on total monomers. Often the blend is formed of 90–99% acrylic acid (some being in salt form) and 1 to 10% of the hydroxyl monomer where $R^1$ is H, $R^2$ is H or $CH_3$ and Y is COO.

Polymers formed solely from the defined carboxylic acid (as free acid and/or salt) and hydroxyl monomers tend to be rather brittle and it is preferred to include in the polymer plasticising monomers. The use of hydroxy alkyl esters containing 6 to 10 carbon atoms will promote platicisation but it is generally desirable to include additional plasticing monomer so as to promote plasticisation and improve flexibility of the resultant polymer. The monomers may be aromatic ethylenically unsaturated monomers, such as acrylonitrile or styrenes (e.g., styrene or substituted styrenes), but they are preferably alkyl esters of (meth) acrylic acid or other suitable unsaturated carboxylic acid. Vinyl acetate and other vinyl esters may be used. The alkyl group of the ester generally contains less than 24 carbon atoms and usually 2 or more. Preferred alkyl groups contain 1 to 10 carbon atoms, especially ethyl and also higher alkyl groups such as 2-ethyl hexyl or other C6–C10 alkyl groups. Particularly preferred plasticising monomers are methyl or ethyl (meth) acrylate, butyl (meth) acrylate and 2-ethyl hexyl (meth) acrylate. The amount is generally 0 to 45% by weight, and is generally at least 2% and often at least 10%. The amount is usually 10 to 30% by weight based on the monomers used for forming the substantially linear polymer.

Other non-ionic monomers that may be used include ethylenically unsaturated monomers that carry a pendant polyalkyleneoxy chain that is terminated by a hydrophobic group containing at least 8 carbon atoms, for instance as described in EP 213799. The use of such monomers, typically in amounts of 1 to 50%, generally 5 to 30%, by weight in the total monomer blend can give improved platicisation, absorptive capacity and non-tackiness, especially in aqueous electrolytes.

After forming the solution of polymer, it can then be shaped and then caused to undergo the internal esterification. Shaping can be by any of the methods described in EP 268498 and thus can be by impregnating or coating the solution on to a film or fibrous core, such as a woven or non-woven sheet or a yarn, filament or film, by using the solution as a laminating material for laminating an absorbent substrate to a sheet substrate by foaming the solution. Preferably however the shaping is by extrusion to provide a shaped element that has one dimension at least five times a second dimension. Thus films and fibres can be made.

The substantially linear, water soluble, polymer may be formed from the monomer blend in any conventional manner. It may be pre-formed and then dissolved to form a polymer solution. For instance it may be made by reverse phase polymerisation if the monomer blend is soluble in water or by water-in-oil emulsion polymerisation if the blend is insoluble in the water, e.g., at a low pH. However this can incur the risk that the polymer may be contaminated by surfactant and this is undesirable. Preferably therefore the polymer is made by aqueous solution or other solution polymerisation methods. It may have been dried, but preferably not. Generally it is formed as a bulk solution by solution polymerisation in the solvent in which it is to be shaped (generally water).

The polymerisation can be conducted in conventional manner in the presence of conventional initiators and/or chain transfer agents to give the desired molecular weight. If the molecular weight of the linear polymer is too low, the physical properties of the article may be inadequate. Generally therefore it is at least 100,000 and preferably at least 500,000 when the article is an extruded film or fibre but lower values, may be suitable in some shaping process, e.g., for casting or coating. If the molecular weight if too high it may be difficult to shape an adequately concentrated solution of the polymer as a fibre or film. Generally the molecular weight is below 1 million, or at the most 2 million. However where the shaped article can initially be relatively thick, e.g., a coarse film or fibre that may then be stretched if it is desired to reduce its thickness, higher molecular weights, e.g., up to 10 million or more, are sometimes suitable.

The solution that is extruded preferably has a viscosity 20° C. of at least 100,000, and usually at least 120,000 cPs. Often it is in the range 150,000 to 200,000 cPs. Higher values are generally unnecessary. All these viscosities are measured at 20° C. using a Brookfield RVT spindle 7 at 20 rpm. The viscosity desirably is also relatively high at the spinning temperature, which typically is elevated, for instance around 80° C. Preferably therefore the solution of 80° C. has a viscosity of at least 5 or 10,000 cPs and most preferably at least 20,000 cPs. For instance it may be in the range 50,000 to 100,000 cPs. These values may be obtained by extrapolation from values obtained using a Brookfield RVT viscometer spindle 7 at 20 rpm at a range of temperature somewhat below 80° C.

Shaping of the solution can involve coating the solution on a surface but generally comprises extruding it as a film or fibre. Substantially immediately after extruding or otherwise shaping the solution the linear polymer is caused to form a uniform solid mixture in the form of an article of the desired shape. The article is initially generally very soft. The conversion of the liquid solution to the soft solid articles can be described as precipitation and may involve solvent evaporation, solvent extraction, or other means of insolubilising the polymer.

The shaping can be by wet spinning into an organic solvent that removes water, generally acetone, methyl-ethyl ketone or other lower ketone, or into an inorganic aqueous salt solution such as of lithium chloride or aluminium sulphate. Acetone is preferred.

Alternatively it can be by dry spinning. Preferably it remains slightly damp until the final cross linking it order to maintain softness. In a particularly preferred method, an aqueous solution of the linear polymer is dry spun at a temperature above 150° C., often above 200° C., typically 200° to 270° C., to give a product that is substantially dry on the surface but contains at least 10% residual moisture, the dry spun product is stretched and is cured by heating, generally after collecting the stretched fibre or film.

The internal esterification and cross linking can be promoted by incorporating a catalyst in a solution of the polymer or by exposing the shaped polymer to a catalyst (e.g., by passing the polymer through an atmosphere or solution of a catalyst for the esterification reaction). Generally however the esterification is conducted in the absence of added catalyst. The monomers can be selected such that the esterification is effected by irradiation but generally it is effected by heating the shaped substantially linear polymer to a temperature above 150° C. for sufficient time for the cross linking reaction to occur. For instanced it may be 170° C. to 200° C. for 5 to 40 minutes. At higher temperatures shorter reaction times are appropriate, for instance 0.1 to 10 minues at 200° to 250° C. or up to 300° C. Preferred esterification conditions generally involve heating to 200° to 220° C. for, for instance, 1 to 3 minutes.

Additional components may be included in the solution that is to be shaped in order to modify the properties of the final product. For instance, external plasticiser may be incorporated. The amount of materials other than the cross-linked polymer is generally below 20%, preferably below 10%, by weight of the final article.

The shaped element often has a minor dimension (e.g., the thickness of the film or diameter of fibre) below 1 mm, usually below 500 $\mu$m and preferably below 250 $\mu$m. However it is usually unnecessary for it to be smaller than 50 $\mu$m. The element can have a relatively short major dimension, for instance 1 mm, e.g., in a fibrid, lamella or flake shaped article but generally the final element is a substantially continuous film, a substantially continuous filament, or staple fibre typically having a length of 3 to 100 mm.

The element usually has a gel capacity of at least 50 g deionised water, and at least 20 g 0.9% NaCl aqueous solution, per gram dry polymer.

The element may be provided with additional surface cross-linking, for instance ionic cross-linking with aluminium or other polyvalent metal compound, in order to improve its rate of absorption of liquids.

The resultant absorbent elements may be used in any environment where it is desirable to absorb water, and in particular aqueous electrolyte such as urine or other body fluids, for instance as a replacement for part of the cellulosic fibres in diapers, catamenial appliances, incontinence pads or bandages. When the articles are in the form of fibres they may be scattered into the cellulosic fibres or a film or, preferably, a woven or non-woven fabric formed of the filaments of fibres may be incorporated in the diaper or other article.

Wound dressing, absorbent wipes and other fabrics may be formed from fibres part of all of which are in accordance with the invention.

Suitable plasticising monomers and their amounts, methods of making the linear polymer, suitable molecular weights and concentrations of the resultant aqueous solution of linear monomer, suitable ways of shaping that solution (e.g., by extrusion or impregnation) and of effecting the subsequent cross linking are all described in more detail above.

The following are some examples.

EXAMPLE 1

A copolymer comprising 75.7% by weight sodium acrylate, 19.3% by weight of acrylic acid, and 5.0% by weight of hydroxypropyl methacrylate was prepared as a 25% by weight solution in water.

The viscosity of this solution was 113,200 cps (Brookfield RVT at 20 rpm spindle 7 at 20° C.). A 100 micron thick film was prepared of this polymer and heated at 200° C. for 5 minutes after which time the polymer was cross linked and absorbed 250 times its own weight of water.

EXAMPLE 2

A copolymer comprising 69.4% by weight sodium acrylate, 17.6% by weight of acrylic acid, 3.0% by weight of hydroxypropyl methacrylate and 10% by weight of methyl acrylate was prepared as a 20% by weight solution in water. The viscosity of this polymer solution was 26,900 cps (Brookfield RVT at 20 rpm spindle 7 at 20° C.). A 100 micron thick film of this polymer cross linked in 2 minutes at 200° C. and 10 minutes at 180° C. to yield a material that absorbed about 200 times its own weight of water.

EXAMPLES 3 to 5

Copolymers were prepared as 20% by weight solutions in water comprising 77.7% by weight of sodium acrylate, 18.8% by weight of acrylic acid and 2.5% by weight of the following monomers.

| Example | Comonomer |
|---|---|
| 3 | Hydroxyethyl methacrylate |
| 4 | Tripropyleneglycol mono acrylate |
| 5 | Glyceryl mono acrylate |

Thin (100 micron) films of these copolymers were prepared and heated at 200° C. for 5 minutes after which time they were cross linked and showed a high capacity for water and 0.9% sodium chloride solution adsorption.

EXAMPLE 6

The process of Example 1 can be repeated by extruding a filament of the polymer as an aqueous solution, optionally containing polyethylene glycol 400 as external plasticiser, into acetone and drawing the filament out of the bath, winding with stretching, and heating. Alternatively the polymer solution can be extruded as a filament into warm air, would while slightly damp and heated.

EXAMPLE 7

A copolymer of composition 69.5/17.5/10/3 parts by weight of sodium acrylate/acrylic acid/methacrylate/hydroxypropyl methacrylate was prepared as a 20% solution in water by polymerisation at 70° C. using azobis cyanovaleric acid as initator. This polymer solution has a Brookfield viscosity at 25° C. (speed 20 rpm Spindle 6) of 275 poise.

Thin films were prepared from 4% solutions of the polymer and heated at 180° C. and 200° C. for various times then tested for solubility by immersing in water for 5 minutes. It was thus determined that 2 minutes at 200° C. or 10 minutes at 180° C. were required to effect cross linking.

A 10% solution of polymer in water was prepared and used to size two yarn samples—1:2/20's count cotton and 2:2/167 decitex 34-filament F34 Trevira textured polyester yarn. The yarns were sized on a Roaches Laboratory Sizing machine using the following conditions.

| | 2/20's count cotton | 2/167 decitex F34 Trevira |
|---|---|---|
| Size Bath temperature (°C.) | 80 | 50 |
| Squeeze pressure (psi) | 12 | 12 |
| Drying cylinder temperatures (°C.) | | |
| 1 | 120 | 110 |
| 2 | 115 | 110 |
| 3 | 110 | 105 |
| Speed (meters min$^{-1}$) | 30 | 30 |

The amount of dry polymer on dry yarn was determined from scour loss to be 10.5% by weight on the cotton yarn and 10.3% by weight on the polyester yarn.

0.5 gram swatches of sized and unsized yarns were then placed in an oven preheated and set at 200° C. for 5 minutes then placed in about 200 mls of deionised water from about 1 hour then squeezed to remove surface water. Each swatch was then reweighed. In this way the amount of water absorbed by the size polymer was determined to be

| | Wt. % water absorbed |
|---|---|
| Sized cotton | 1255 |
| Untreated cotton | 48 |
| Sized Polyester | 1033 |
| Untreated Polyester | 84 |

EXAMPLE 8

A copolymer was formed of 75.7% sodium acrylate, 19.3% acrylic acid and 5% hydroxyethyl acrylate. An aqueous solution of this can be printed on to a paper tissue. A second tissue can then be applied on to the printed surface while set and the laminate heated to cause cross linking.

EXAMPLE 9

A copolymer was formed of 3% hydroxy propylmethacrylate, 40% methyl acrylate and 57% acrylic acid which was 75% sodium acrylate and 25% free acrylic acid. The polymer was made as an aqueous solution of about 35% polymer concentration, and had a molecular weight of around 500,000.

The viscous polymer solution was dry spun through a lubricated, multiple orifice, spinnerette into a temperature of about 250° C. and the fibres were stretched and immediately wound up. They were dry on the surface but contained residual moisture within their structure. Quite quickly after being spun the fibres were cured at 210° C. for 2 minutes. The resultant product was a flexible, high absorbent, fibre.

In alternative processes the amount of methyl acrylate can be reduced to, for instance, 25% and/or methyl or other alkyl methacrylate can be used.

EXAMPLE 10

50 gms of a 40% wt/wt solution of a copolymer comprising 43% sodium acrylate, 17% acrylic acid, 37% methyl acrylate and 3% hydroxypropyl methacylate by weight in water of Brookfield viscosity 60,000 cps (at 10 rpm) was mixed with 50 gms of water and adjusted to a temperature of 40° C. 100 gms of a hydrophilic polyether polyisocyanate Hypol RHP 2000 (Grace Rexoline Chemicals Hypol is a trade mark) were rapidly mixed in and the foam expanded over a period of about 2 minutes to a volume of about 400 mls. The foam was then baked for 30 minutes to ensure complete reaction. A small piece of this foam was cut off and immersed in cold tap water. It swelled over a period of 2 minutes to about 20 times its original volume. The excess water was squeezed out and the foam dried at 100° C. for 2 hours when is reduced to its original volume. It was again swollen with water to about 20 times its original volume.

EXAMPLE 11

Three copolymer solutions in water were prepared (1, 2 and 3) from monomers containing 1, 2 and 3% by weight respectively of hexapropylene glycol monomethyacrylate. The rest of each copolymer comprised 20% by weight of methyl acrylate and the balance was 75 mole % neutralised sodium acrylate/acrylic acid. The polymer concentrations of the solution (as weight %) and solution viscosity (Brookfield RVT at 20 rpm spindle 7 at 20° C.—in cp) for polymers 1, 2 and 3 were respectively 33.6 and 214,000, 32.3 and 136,000 and 35.3 and 162,000. Approximately 100 micron thick films of these polymers were prepared and heated for various times at 220° C. to effect cross linking. The free swell, retention and % by weight soluble polymer in 0.9% sodium chloride solution for each heat treated film were determined and are given in the following table:

| Time at 220° C. (minutes) | Polymer 1 | | | Polymer 2 | | | Polymer 3 | | |
|---|---|---|---|---|---|---|---|---|---|
| | FS | RET | PSP | FS | RET | PSP | FS | RET | PSP |
| 0.5 | | | | | | | 16 | 15 | 80 |
| 1 | | | | | | | 24 | 23 | 80 |
| 2 | | | | 16 | 13 | 50 | 34 | 33 | 42 |
| 4 | | | | | | | 53 | 52 | 25 |
| 5 | 32 | 30 | 49 | 55 | 52 | 35 | 59 | 57 | 21 |
| 7.5 | | | | 61 | 56 | 24 | | | |
| 10 | 46 | 43 | 19 | 44 | 39 | 19 | 42 | 35 | 16 |
| 12 | | | | | | | 34 | 23 | 12 |
| 15 | 55 | 50 | 16 | 32 | 24 | 12 | | | |
| 20 | 51 | 44 | 12 | | | | | | |
| 25 | 38 | 24 | 7 | | | | | | |

FS = Free swell (gm/gm)
RET = Retention (gm/gm)
PSP = Precentage soluble polymer (% w/w)

EXAMPLE 12

Three copolymers were prepared (1, 2 and 3) from monomers containing 1, 2 and 3% by weight respectively of hexapropylene glycol monomethacrylate. The rest of the copolymer comprised 20% by weight of methyl acrylate and the balance was 75 mole % neutralised sodium acrylate/acrylic acid.

three further copolymers 4, 5 and 6 were produced in the same way from monomers containing 1, 2 and 3% respectively of hydroxy propylmethacrylate with the same amounts of methyl acrylate, sodium acrylate and acrylic acid as before.

All the polymer solutions were prepared to give a similar molecular weight and distribution at a concentration of 33.0% by weight and viscosities between 1000 and 1200 poise.

Approximately 100 micron thick films of these polymers were prepared and heated for varous times ranging from 1 minute up to 25 minutes at 220° C. to effect cross linking. In each instance the time was selected by experiment to give the maximum free swell value.

The free swell, retention and % by weight of soluble polymer in 0.9% sodium chloride solution for each heat treated film were determined. From this data are summarised the figures in the table below. These results clearly show that polymer prepared using hexapropylene glycol monomethacrylate achieve a higher capacity for adsorption than polymers prepared using hydroxypropyl methacrylate.

| Polymer | Free Swell (gm/gm) | Retention (gm/gm) | Time @ 220° C. (mins) |
|---|---|---|---|
| 1 | 55 | 50 | 15 |
| 2 | 62 | 59 | 7 |
| 3 | 62 | 59 | 6 |
| 4 | 43 | 36 | 14 |
| 5 | 48 | 40 | 8 |
| 6 | 48 | 46 | 5 |

What is claimed is:

1. An extruded, water absorbent, water insoluble polymeric element that has a gel capacity of at least 50 grams deionized water per gram dry polymer and that is in the form of fibre or film, wherein the polymer is a cross linked copolymer of a water soluble blend of ethylenically unsaturated monomers comprising a monomer that provides carboxylic acid groups and a monomer that is a hydroxy alkyl ester of a carboxylic monomer, and in which the cross links are ester linkages formed between the carboxylic acid groups and the hydroxy alkyl ester groups.

2. An element according to claim 1 in which the monomer that provides the carboxylic acid groups is selected from acrylic acid and water soluble salts thereof.

3. An element according to claim 1 in which the hydroxy alkyl esters are of (meth) acrylic acid.

4. An element according to claim 1 in which the carboxylic acid monomer is present as a mixture of free carboxylic acid and alkali metal salt groups in the ratio 1:1 to 1:10 and the total amount thereof is at least 40% by weight of the monomers.

5. An element according to claim 4 in which the carboxylic acid is acrylic acid, the hydroxy alkyl esters are of (meth) acrylic acid and in which the monomer blend includes from 10 to 45% by weight of plasticizing monomer selected from $C_{1-24}$ alkyl (meth) acrylate.

6. An element according to claim 1 in which the monomer blend includes 2 to 50% by weight plasticizing monomer.

7. An element according to claim 6 in which the plasticizing monomer is selected from styrenes, vinyl esters, acrylonitrile and alkyl esters or ethylenically unsaturated acid.

8. An element according to claim 6 in which the plasticising monomer is selected from $C_{1-24}$ alkyl (meth) acrylates in an amount of from 10 to 45% by weight of the monomers.

9. An element according to claim 1 in which the monomer blend comprises at least 50% by weight carboxylic acid monomer, 0.1 to 15% hydroxy alkyl esters of vinyl carboxylic monomers, and up to 50% plasticising monomer selected from styrenes, vinyl esters, acrylonitrile and alkyl esters of ethylenically unsaturated acids.

10. An element according to claim 1 in which the blend comprises at least 50% by weight (meth) acrylic acid or water soluble salt thereof, 1 to 10% by weight hydroxy alkyl ester of (meth) acrylic acid and 10 to 45% by weight $C_{1-24}$ alkyl (meth) acrylate.

11. An element according to claim 1 in which the fibre or film is stretched before the formation of the cross linkages.

12. In a polymeric element formed of a cross linked copolymer of a water soluble blend of ethylenically unsaturated monomers comprising at least 50% by weight of a monomer that provides carboxylic acid groups and a monomer that is a hydroxy alkyl ester of a carboxylic monomer, and in which the cross links are ester linkages formed between the carboxylic acid groups and the hydroxy alkyl ester groups, the improvement in which the element is an extruded water absorbent water insoluble fibre or film that has a gel capacity of at least 50 grams deionised water per gram dry polymer.

13. An element according to claim 12 in which the monomer that provides the carboxylic acid groups is a mixture of free acrylic acid and water soluble alkali metal salts thereof in a ratio of 1:1 to 1:10 and the total amount thereof is at least 50% by weight of the monomers, the hydroxy alkyl esters are of (meth) acrylic acid, and in which the monomer blend includes 10 to 45% by weight of the monomers of plasticising monomer selected from $C_{1-24}$ alkyl (meth) acrylates.

14. In a polymeric element formed of a cross linked copolymer of a water soluble blend ethylenically unsaturated monomers comprising a monomer that provides at least 50% by weight carboxylic acid groups and a 0.1 to 15% by weight of a monomer that is a hydroxy alkyl ester of a carboxylic monomer, and in which the cross links are ester linkages formed between the carboxylic acid groups and the hydroxy alkyl ester groups, the improvement in which the element is an extruded water absorbent water insoluble fibre or film that has a gel capacity of at least 50 grams deionised water per gram dry polymer and which has been made by extruding a linear copolymer of the said blend in the form of the fibre or film and then forming the said ester cross linkages between the carboxylic acid groups and the hydoxy alkyl ester groups.

15. An element according to claim 14 in which the monomer that provides the carboxylic acid groups is a mixture of free acrylic acid and water soluble alkali metal salts thereof in a ratio of 1:1 to 1:10 and the total amount thereof is at least 50% by weight of the monomers, the hydroxy alkyl esters are of (meth) acrylic acid, and which the monomer blend includes 10 to 45% by weight of the monomers of plasticising monomer selected from $C_{1-24}$ alkyl (meth) acrylates.

16. An extruded, water absorbent, water insoluble polymeric element that has a gel capacity of at least 50 grams deionised water per gram dry polymer and that is in the form of fibre or film, wherein the polymer is a cross linked copolymer of a water soluble blend of ethylenically unsaturated monomers comprising at least 50% by weight of a monomer that provides carboxylic acid groups and 0.1 to 15% by weight of a hydroxylic monomer that provides hydroxyl groups and that has the formula $CHR^1\!=\!CR^2\!-\!Y\!-\!Ma\!-\!OH$ where $R^1$ is hydrogen or carboxy, $R^2$ is hydrogen, carboxy or methyl, Y is O, $CH_2O$ or COO, M is alkyleneoxy and a is at least 5 and in which the cross links are linkages formed between the carboxylic acid groups and the said hydroxyl groups.

17. In a polymeric element formed of a cross linked copolymer of a water soluble blend of ethylenically unsaturated monomers comprising at least 50% by weight of a monomer that provides carboxylic acid groups and 0.1 to 15% by weight of a hydroxylic monomer that provides hydroxyl groups and that has the formula $CHR^{1'}CR^2\!-\!Y\!-\!Ma\!-\!OH$ where $R^1$ is hydrogen or carboxy, $R^2$ is hydrogen, carboxy or methyl, Y is O, $CH_2O$ or COO, M is alkyleneoxy and a is at least 5, and in which the cross links are linkages formed between the carboxylic acid groups and the said hydroxyl groups, the improvement in which the element is an extruded water absorbent water insoluble fibre or film that has a gel capacity of at least 50 grams deionised water per gram dry polymer.

18. A water absorbent, water insoluble, polymeric element having a gel capacity of at least 50 grams deionised water per gram dry polymer and that has been made by a process comprising providing a solution of a water soluble, substantially linear, polymer that has been made be copolymerisation of a water soluble blend of monoethylenically unsaturated monomers comprising at least 50% by weight carboxylic monomer that provides carboxyl groups and 0.1 to 15% by weight hydroxylic monomer that provides hydroxyl groups and that has the formula $CHR^{1'}CR^2\!-\!Y\!-\!M_a\!-\!OH$ where $R_1$ is hydrogen or carboxy, $R^2$ is hydrogen, carboxy or methyl, Y is O, $CH_2O$ or COO, M is alkyleneoxy and a is at least 5, shaping the solution by a shaping step selected from extrusion, coating, impregnation and foaming to shape the linear polymer into the shape of the desired element, and then heating the shaped element to cause the said carboxylic and hydroxylic groups to react in the shaped element to form cross linkages of the formula $-Y-M_a-OCO-$ where Y, M and a are as defined above.

19. An element according to claim 18 in which the monomer blend contains 10 to 45% by weight plasticising monomer selected from alkyl esters of ethylenically unsaturated acids, acrylonitriles, styrenes, and vinyl esters.

20. An element according to claim 18 in which $R^1$ is hydrogen, $R^2$ is hydrogen or methyl, M is selected from ethyleneoxy, propyleneoxy and butyleneoxy, Y is COO and a is from 5–100.

21. An element according to claim 20 in which the blend comprises 0.1 to 10% by weight of the hydroxylic monomer, 50 to 89.9% by weight acrylic acid (or water soluble salt thereof) and 10 to 30% by weight methyl acrylate.

22. An element according to claim 18 in which $M_a$ is hexapropyleneoxy.

23. In a water absorbent, water insoluble, polymeric element having a gel capacity of at least 50 grams deionised water per gram dry polymer and that has been made by a process comprising providing a solution of a water soluble, substantially linear, polymer that has been made by copolymerisation of a water soluble blend of monoethylenically unsaturated monomers comprising at least 505 by weight carboxylic monomer that provides carboxyl groups and 0.1 to 15% by weight hydroxylic monomer that provides hydroxyl groups and that has the formula $CHR^{1'}CR^2$—Y—$M_a$—H where $R^1$ is hydrogen or carboxy, $R^2$ is hydrogen, carboxy or methyl, Y is O, $CH_2O$ or COO, and M is alkyleneoxy, shaping the solution by a shaping step selected from extrusion, coating, impregnation and foaming to shape the linear polymer into the shape of the desired element, and then heating the shaped element to cause the said carboxylic and hydroxylic groups to react in the shaped element to form cross linkages of the formula —Y—$M_a$—QCO— where Y, M and a are as defined above, the improvement which comprises a being at least 5.

* * * * *